US012595282B1

(12) United States Patent
Wei et al.

(10) Patent No.: US 12,595,282 B1
(45) Date of Patent: Apr. 7, 2026

(54) METHOD FOR SYNTHESIZING NUCLEOTIDE STRANDS

(71) Applicant: HONGENE BIOTECH PTE. LTD., Singapore (SG)

(72) Inventors: Minzhi Wei, Singapore (SG); Zhipeng Chen, Singapore (SG)

(73) Assignee: HONGENE BIOTECH PTE. LTD., Singapore (SG)

( * ) Notice: Subject to any disclaimer, the term of this patent is extended or adjusted under 35 U.S.C. 154(b) by 0 days.

(21) Appl. No.: 19/251,872

(22) Filed: Jun. 27, 2025

(30) Foreign Application Priority Data

Jan. 23, 2025 (CN) .......................... 202510110953.1

(51) Int. Cl.
| | |
|---|---|
| *C07H 21/02* | (2006.01) |
| *C07H 1/00* | (2006.01) |
| *C07H 21/04* | (2006.01) |

(52) U.S. Cl.
CPC .............. *C07H 21/02* (2013.01); *C07H 1/00* (2013.01); *C07H 21/04* (2013.01)

(58) Field of Classification Search
None
See application file for complete search history.

(56) References Cited

PUBLICATIONS

Haoqiang Shi, Yanchao Huang, Qi Gan, Mianwen Rui, Hongxun Chen, et al.. Biochemical characterization of a thermostable DNA ligase from the hyperthermophilic euryarchaeon Thermococcus barophilus Ch5. Applied Microbiology and Biotechnology, 2019, ff10.1007/s00253-019-09736-9ff. ffhal02091415f.*

* cited by examiner

*Primary Examiner* — Patrick T Lewis

(74) *Attorney, Agent, or Firm* — Bayramoglu Law Offices LLC

(57) ABSTRACT

The present disclosure discloses a method for synthesizing nucleotide strands, relating to the biology field. The synthesizing method includes regulating a temperature for synthesizing the nucleotide strands to ≥42° C. or performing a procedure of high-temperature denaturation-low-temperature annealing for at least one time during the synthesis, thus achieving efficient ligation of natural nucleic acid fragments and/non-natural nucleic acid fragments. This method can effectively reduce byproducts produced during the synthesis of nucleotide strands, improve the efficiency of synthesis of nucleotide strands of interest, and facilitate large-scale production of high-quality nucleotide strands.

20 Claims, 1 Drawing Sheet
Specification includes a Sequence Listing.

F1                                              F2

SS: 5' | Pho-A-C-G-C-A-U | G-A-A-C-U-G-C-U-A-C-U-U-A-U-C-A | 3'
AS: 3' | U-G-C-G-U-A-C-U-U-G-A | C-G-A-U-G-A-A-U-A-G-U | 5'

SS: 5' | VP-mA-fC-mG-fC-mA-dT-fG-mA | msA-fC-mU-msG-fC-mU-fsA-mC-fU-mU-mA-fU-msC-fA | 3'
AS: 3' | mU-mG-mC-fG-mU-fA-mC-fU-mU-fG-msA | mC-fG-mA-dU-mG-fA-mA-fU-mA-fG-mU | 5'

SS: 5' | VP-mA – mG –mC –mC–msU– fU-mA-mA | –mA –mU –mA –fC – fA – fA –mU –mA – mU– mU –mA–mA–mG–mC–mG–mA | 3'
AS: 3' | msU- mC- fG – mG- mA- mA-fU- mU- mU- mA- fU- | mG-mU-mU- mA-msU-msA-msA- fU- mU-mC-mG-mC-mU | 5'

FIG. 3

SEQUENCE LISTING

```
Sequence total quantity: 14
SEQ ID NO: 1              moltype = AA   length = 334
FEATURE                  Location/Qualifiers
source                   1..334
                         mol_type = protein
                         organism = synthetic construct
SEQUENCE: 1
MFKKYSSLEN HYNSKFIEKL YSLGLTGGEW VAREKIHGTN FSLIIERDKV TCAKRTGPIL   60
PAEDFFGYEI ILKNYADSIK AVQDIMETSA VVSYQVFGEF AGPGIQKNVD YCDKDFYVFD  120
IIVTTESGDV TYVDDYMMES FCNTFKFKMA PLLGRGKFEE LIKLPNDLDS VVQDYNFTVD  180
HAGLVDANKC VWNAEAKGEV FTAEGYVLKP CYPSWLRNGN RVAIKCKNSK FSEKKKSDKP  240
IKAKVELSEA DNKLVGILAC YVTLNRVNNV ISKIGEIGPK DFGKVMGLTV QDILEETSRE  300
GITLTQADNP SLIKKELVKM VQDVLRPAWI ELVS                             334

SEQ ID NO: 2              moltype = AA   length = 334
FEATURE                  Location/Qualifiers
source                   1..334
                         mol_type = protein
                         organism = synthetic construct
SEQUENCE: 2
MFKKYSSLEN HYNSKFIEKL YSLGLTGGEW VAREKIHGTN FSLIIERDKV TCAKRTGPIL   60
PAEDFFGYEI ILKNYADSIK AVQDIMETSA VVSYQVFGEF AGPGIQKNVD YGDKDFYVFD  120
IIVTTESGDV TYVDDYMMES FCNTFKFKMA PLLGRGKFEE LIKLPNDLDS VVQDYNFTVD  180
HAGLVDANKC VWNAEAKGEV FTAEGYVLKP CYPSWLRNGN RVAIKCKNSK FSEKKKSDKP  240
IKAKVELSEA DNKLVGILAC YVTLNRVNNV ISKIGEIGPK DFGKVMGLTV QDILEETSRE  300
GITLTQADNP SLIKKELVKM VQDVLRPAWI ELVS                             334

SEQ ID NO: 3              moltype =    length =
SEQUENCE: 3
000

SEQ ID NO: 4              moltype = RNA   length = 14
FEATURE                  Location/Qualifiers
source                   1..14
                         mol_type = other RNA
                         organism = synthetic construct
SEQUENCE: 4
actgctactt atca                                                   14

SEQ ID NO: 5              moltype = RNA   length = 11
FEATURE                  Location/Qualifiers
source                   1..11
                         mol_type = other RNA
                         organism = synthetic construct
SEQUENCE: 5
tgataagtag c                                                      11

SEQ ID NO: 6              moltype = RNA   length = 11
FEATURE                  Location/Qualifiers
source                   1..11
                         mol_type = other RNA
                         organism = synthetic construct
SEQUENCE: 6
```

-continued

```
agttcatgcg t                                                    11

SEQ ID NO: 7          moltype =   length =
SEQUENCE: 7
000

SEQ ID NO: 8          moltype = RNA  length = 14
FEATURE               Location/Qualifiers
source                1..14
                      mol_type = other RNA
                      organism = synthetic construct
SEQUENCE: 8
actgctactt atca                                                 14

SEQ ID NO: 9          moltype = RNA  length = 11
FEATURE               Location/Qualifiers
source                1..11
                      mol_type = other RNA
                      organism = synthetic construct
SEQUENCE: 9
tgataagtag c                                                    11

SEQ ID NO: 10         moltype = RNA  length = 11
FEATURE               Location/Qualifiers
source                1..11
                      mol_type = other RNA
                      organism = synthetic construct
SEQUENCE: 10
agttcatgcg t                                                    11

SEQ ID NO: 11         moltype =   length =
SEQUENCE: 11
000

SEQ ID NO: 12         moltype = RNA  length = 16
FEATURE               Location/Qualifiers
source                1..16
                      mol_type = other RNA
                      organism = synthetic construct
SEQUENCE: 12
atacaatatt aagcga                                               16

SEQ ID NO: 13         moltype = RNA  length = 13
FEATURE               Location/Qualifiers
source                1..13
                      mol_type = other RNA
                      organism = synthetic construct
SEQUENCE: 13
tcgcttaata ttg                                                  13

SEQ ID NO: 14         moltype = RNA  length = 11
FEATURE               Location/Qualifiers
source                1..11
                      mol_type = other RNA
                      organism = synthetic construct
SEQUENCE: 14
tatttaaggc t                                                    11
```

METHOD FOR SYNTHESIZING NUCLEOTIDE STRANDS

CROSS-REFERENCE TO RELATED APPLICATION

This application is based upon and claims priority to Chinese Patent Application No. 202510110953.1, filed on Jan. 23, 2025, the entire contents of which are incorporated herein by reference.

SEQUENCE LISTING

The instant application contains a Sequence Listing which has been submitted in XML format via EFS-Web and is hereby incorporated by reference in its entirety. Said XML copy is named GBCF102-Track-One_Sequence-_Listing.xml, created on Jun. 26, 2025, and is 11,683 bytes in size.

TECHNICAL FIELD

The present disclosure relates to the biology field, and specifically to a method for synthesizing nucleotide strands.

BACKGROUND ART

RNA-based drugs are a novel type of drugs that have attracted significant attention in recent years, and have been widely explored in the field for treatment of various diseases, such as tumors, rare diseases, gastrointestinal diseases, cardiovascular diseases and metabolic disorders. Compared with the conventional research and development of small molecular drugs and protein drugs, RNA-based drugs have many advantages, including rapid research, development and synthesis, high target specificity, and highly customization, among others. RNA-based drugs substantially can be divided into four categories: RNA aptamers, antisense nucleotide (antisense oligonucleotide, ASO) drugs, RNA interference (miRNA and siRNA) drugs and messenger RNA (mRNA) drugs. In addition to serving as RNA-based drugs, RNA also plays an important role in gene editing techniques. In the widely used CRISPR-Cas gene editing technique, single guide RNA (gRNA) can form a complex with DNA endonuclease Cas, and locate a genomic loci to be edited by complementary pairing, thereby initiating a Cas-mediated gene editing process. With the rise of RNA products in the pharmaceutical field, the demand for RNA synthesis has been increasing year by year.

At present, for chemical synthesis of nucleotide strands, nucleotide residues are generally serially linked and extended in sequence, with 1 base each time, to prepare nucleotide strands of interest. Since the efficiency of chemical synthesis reaction of nucleotide strands cannot reach 100%, product purity and yield of target product of synthesized nucleotide strands of interest both decrease with the increase of length of the nucleotide strands of interest, resulting in that a synthesized product contains a certain amount of non-target nucleotide strands whose length does not accord with that of the nucleotide strands of interest.

For nucleotide strands with a length less than or equal to 20 nt, a proportion of nucleotide strands of interest finally in a synthesized product can be increased by a purification process (for example, ion exchange column or reverse phase column, etc). However, since the length of a part of the non-target nucleotide strands is relatively close to the length of the nucleotide strands of interest (for example, the length of the non-target nucleotide strands only differs from the length of the nucleotide strands of interest by 1 nt or 2 nt), these non-target nucleotide strands are quite close to the nucleotide strands of interest in property, so that these non-target nucleotide strands cannot be effectively separated or removed from the synthesized product. For nucleotide strands greater than 20 nt in length, particularly nucleotide strands greater than 50 nt in length, and even nucleotide strands greater than 100 nt in length, after chemical synthesis thereof, more non-target nucleotide strands cannot be effectively separated or removed from the synthesized product.

The presence of the non-target nucleotide strands in the synthesized product often affects function, activity, etc. of target nucleotide strands, and particularly for cases where the nucleotide strands of interest are antisense drugs, RNAi drugs, nucleic acid aptamer drugs, sgRNA drugs, etc., the presence of the non-target nucleotide strands seriously affects the nucleotide strands of interest in exerting efficacy thereof.

In view of this, the present disclosure is specifically proposed.

SUMMARY

The present disclosure aims at providing a method for synthesizing nucleotide strands.

The present disclosure is implemented as follows.

In the first aspect, embodiments of the present disclosure provide a method for synthesizing a nucleotide strand of interest, comprising: performing a ligation reaction on a nicked double-stranded nucleic acid molecule and/or a nucleic acid substrate capable of forming the nicked double-stranded nucleic acid molecule under a condition of a first set temperature, where the first set temperature is ≥42° C.

In the second aspect, embodiments of the present disclosure provide a method for synthesizing a nucleotide strand of interest, comprising: performing a ligation reaction on a nicked double-stranded nucleic acid molecule and/or a nucleic acid substrate capable of forming the nicked double-stranded nucleic acid molecule, wherein during the ligation reaction, the procedure of high-temperature denaturation-low-temperature annealing according to the preceding embodiments.

The present disclosure has the following beneficial effects.

By regulating a temperature for synthesizing the nucleotide strand of interest to ≥42° C. or performing the procedure of high-temperature denaturation-low-temperature annealing for at least one time during the synthesis, the present disclosure achieves efficient ligation of natural nucleic acid fragments and/or non-natural nucleic acid fragments, reduces byproducts produced during the synthesis of nucleotide strands, improves the efficiency of synthesis of nucleotide strands of interest, and facilitates large-scale production of high-quality nucleotide strands.

BRIEF DESCRIPTION OF DRAWINGS

In order to more clearly illustrate technical solutions of embodiments of the present disclosure, drawings which need to be used in the embodiments will be briefly introduced below. It should be understood that the drawings merely show some embodiments of the present disclosure, and thus should not be considered as limitation to the scope, and those ordinarily skilled in the art still could obtain other relevant drawings according to the drawings, without using any inventive efforts.

FIG. 1 is a schematic diagram of nucleic acid substrates used in Examples 1-5 after ligation;

FIG. 2 is a schematic diagram of nucleic acid substrates used in Example 6 after ligation; and FIG. 3 is a schematic diagram of nucleic acid substrates used in Example 7 after ligation.

DETAILED DESCRIPTION OF EMBODIMENTS

In order to make objectives, technical solutions and advantages of embodiments in the present disclosure clearer, the technical solutions in the embodiments of the present disclosure will be described clearly and completely below. Embodiments, for which no concrete conditions are specified, are carried out according to conventional conditions or conditions recommended by manufactures. Where manufacturers of reagents or instruments used are not specified, they are conventional products commercially available.

In the description below, many professional terms are used. In order to have a clearer and consistent understanding of the description and claims, including specified scopes of these terms, the following definitions are provided.

Oligonucleotide: it generally refers to a linear polynucleotide fragment composed of 2-10 nucleotide residues linked by phosphodiester bonds. However, it should be noted that the number of nucleotides of an oligonucleotide is not strictly specified, and in some literature, polynucleotide molecules containing 30 or more, up to 200, 300, 400, or 500 nucleotide residues may also be referred to as oligonucleotides.

Natural ribonucleotide: it is naturally occurring ribonucleotide composed of one molecule of phosphoric acid, one molecule of ribose (a pentose sugar), and one molecule of nitrogenous base. Depending on kinds of nitrogenous bases, natural ribonucleotides are divided into adenine ribonucleotides, guanine ribonucleotides, cytosine ribonucleotides, and uracil ribonucleotides. 2'-deoxyribonucleotide: it consists of one molecule of phosphoric acid, one molecule of 2'-deoxyribose (deoxylation of 2' of ribose, being a hydrogen atom), and one molecule of nitrogenous base. Depending on types of nitrogenous bases, natural 2'-deoxyribonucleotides are divided into adenine deoxyribonucleotides, guanine deoxyribonucleotides, cytosine deoxyribonucleotides, and thymine deoxyribonucleotides.

Non-natural nucleotide: it refers to a nucleotide after modification of the phosphate group, nitrogenous base, sugar ring and glycosidic bond of a natural nucleotide.

RNA: it refers to a molecule formed by natural or non-natural ribonucleotides linked by phosphoester bonds. Although typical RNA molecules are linked together by standard phosphodiester bonds, therapeutic RNAs may contain one or more non-standard bonds. RNA may be single-stranded or double-stranded, or may include both single-stranded and double-stranded regions. In addition, ribonucleotides can also be classified into linear ribonucleotide strands and circular ribonucleotide strands according to their morphology. The circular RNA (circRNA) is RNA that is formed by one or more linear ribonucleotide strands linked head-to-tail by phosphoester bonds, and has a closed circular structure.

The term "modified RNA" refer to a RNA molecule containing at least one Non-natural non-natural ribonucleotides.

The term "DNA" refer to a molecule formed by 2'-deoxyribonucleotides linked by phosphoester bonds.

The term "modified DNA" refer to a DNA molecule containing at least one non-natural 2'-deoxyribonucleotide with modifications of the phosphate group, nitrogenous base, sugar ring and glycosidic bond of a natural 2'-deoxyribonucleotides.

As used herein, "wild-type" refers to a form found in nature. For example, a wild-type protein sequence refers to a form that is found in nature, and can be isolated from a source in nature and has not been intentionally modified or altered by human.

The term "nick" herein refers to absence of a phosphodiester bond between two adjacent nucleotide fragments in a double-stranded structure. An intact phosphodiester bond may be formed by catalyzing the nick sealed with a double-stranded ligase, that is, an intact phosphodiester bond is formed between a 3'-hydroxyl group of one nucleotide unit at the nick and a 5'-monophosphate group of the other nucleotide unit at the nick, which is catalyzed by the double-stranded ligase. "Nick" can also be understood as a notch formed in a double-stranded nucleic acid molecule due to cleavage of a phosphodiester bond.

The term "gap" herein refers to such a case that a certain strand in a double-stranded structure is broken into two strands due to deletion of one or more contiguous nucleotides, and the two strands form a gap relationship.

A nucleic acid substrate herein refers to oligonucleotides capable of forming nicked double-stranded nucleic acid molecules, where the oligonucleotides contain a 5'-monophosphate group and/or a 3'-hydroxyl group.

The term "denaturation" herein refers to a process of disrupting a hydrogen bond between base pairs of double-stranded nucleic acids such as double-stranded DNA, double-stranded RNA or DNA/RNA through high-temperature incubation, causing the double-stranded nucleic acid to become single-stranded nucleic acid.

The term "annealing" herein refers to a process of gradually cooling a nucleic acid solution having undergone high-temperature denaturation to a low temperature to convert single-stranded nucleic acid into double-stranded nucleic acid.

The term "sequence identity" (%) as used herein refers to comparisons among polynucleotides and polypeptides, and is determined by comparing two optimally aligned sequences over a comparison window, where a portion of a polynucleotide or polypeptide sequence in the comparison window may include insertionsor deletions (i.e., gaps) as compared to a reference sequence for optimal alignment of the two sequences. The percent may be calculated by determining the number of positions at which an identical nucleic acid base or amino acid residue occurs in two sequences to yield the number of matched positions, dividing the number of matched positions by the total number of positions in the comparison window, and multiplying the result by 100 to yield the percent sequence identity. Alternatively, the percent may be calculated by determining the number of positions at which either identical nucleic acid base or amino acid residue occurs in two sequences or the number of positions at which a nucleic acid base or amino acid residue is aligned with a gap to yield the number of matched positions, dividing the number of matched positions by the total number of positions in the comparison window, and multiplying the result by 100 to yield the percent sequence identity. Those skilled in the art could appreciate that there are currently many algorithms available to align sequences, such as the Smith-Waterman

5 local homology algorithm (Smith and Waterman, Adv. Appl. Math., 2:482 [1981]) and Needleman-Wunsch global homology alignment algorithm (Needleman and Wunsch, J. Mol. Biol., 48:443 [1970]). These algorithms have been designed into relevant software by which researchers in the field can quickly align protein sequences or nucleotide sequences, such as the European Bioinformatics Institute (EMBL-EBI) open software EMBOSS Water (https://www.ebi.ac.uk/jdis-patcher/psa/emboss_water) based on the Smith-Waterman algorithm and EMBOSS needle software (https://www.ebi.ac.uk/jdispatcher/psa/emboss_needle) based on the Needleman-Wunsch algorithm. Protein sequence alignment and sequence alignment identity % may be performed using the open software EMBOSS Water software. A scoring matrix employed during the alignment is BLOSUM62, with gap opening score (GAP OPEN) set to 10, and gap extension score (GAP EXTEND) set to 1.

"Reference sequence" refers to a specified sequence used as a basis for sequence comparison. The reference sequence may be a subset of a large sequence, e.g., a segment of a full-length gene or polypeptide sequence. Generally, a reference sequence is at least 20 nucleotides or amino acid residues in length, at least 25 residues in length, at least 50 residues in length, at least 100 residues in length, or a full length of a nucleic acid or polypeptide. As two polynucleotides or polypeptides may each (1) contain a sequence (i.e., a portion of a complete sequence) that is similar between two sequences, and (2) may further contain a sequence that is divergent between two sequences, sequence comparison between two (or more) polynucleotides or polypeptides is typically performed by comparing sequences of the two polynucleotides or polypeptides over the "comparison window" so as to identify and compare local regions of sequence similarity. In some embodiments, the "reference sequence" can be based on a primary amino acid sequence, where the reference sequence is a sequence that can have one or more changes in the primary sequence.

The "comparison window" refers to a conceptual segment of at least approximately 20 contiguous nucleotide positions or amino acid residues where a sequence may be compared with a reference sequence of at least 20 contiguous nucleotides or amino acids, and where the portion of the sequence in the comparison window may include additions or deletions (i.e., gaps) of 20% or less as compared to the reference sequence (which does not include additions or deletions) for optimal alignment of the two sequences. The comparison window can be longer than 20 contiguous residues, and includes, optionally 30, 40, 50, 100, or longer windows.

Specific Technical Solutions

In one aspect, embodiments of the present disclosure provide a method for synthesizing a nucleotide strands, including: performing a ligation reaction on a nicked double-stranded nucleic acid molecule and/or one or more nucleic acid substrates capable of forming the nicked double-stranded nucleic acid molecule under a condition of a first set temperature, where the first set temperature is ≥42° C.

In some embodiments, the first set temperature specifically may be any one or within a range between any two of 42, 45, 48, 50, 52, 55, 57, and 60° C.

In some embodiments, reaction duration under the condition of the first set temperature is ≥30 s.

In some embodiments, the reaction duration under the condition of the first set temperature ranges from 5 min to 16 h, and specifically may be any one or within a range between any two of 5 min, 10 min, 15 min, 20 min, 25 min, 30 min, 35 min, 40 min, 45 min, 50 min, 55 min, 60 min, 1 h, 2 h, 3 h, 4 h, 5 h, 6 h, 7 h, 8 h, 9 h, 10 h, 11 h, 12 h, 13 h, 14 h, 15 h, and 16 h.

In some embodiments, before, during and/or after the reaction under the condition of the first set temperature, the synthesizing method further includes performing a procedure of high-temperature denaturation-low-temperature annealing for at least one time, where the high-temperature denaturation includes performing a first incubation at a second set temperature, the second set temperature ≥ the first set temperature; and the low-temperature annealing includes performing a second incubation at a third set temperature, the third set temperature < the second set temperature.

In some embodiments, the second set temperature ranges from 42° C. to 60° C., and specifically may be any one or within a range between any two of 42, 44, 45, 46, 48, 50, 52, 54, 56, 58, and 60° C.

In some embodiments, the third set temperature is ≥4° C.

In some embodiments, the third set temperature is ≥ any one of 4, 5, 6, 8, 10, 12, 14, 16, 18, 20, 22, 24, 26, 28, 30, 32, 34, 36, 38, and 40° C.

In some embodiments, the synthesizing method further includes: performing the procedure of high-temperature denaturation-low-temperature annealing for two or more times.

The term "two or more times" as mentioned includes both exactly twice and any number of times greater than twice.

In some embodiments, duration of the first incubation is ≥30 s.

In some embodiments, the duration of the first incubation ranges from 5 min to 16 h, and specifically may be any one or within a range between any two of 5 min, 10 min, 15 min, 20 min, 25 min, 30 min, 35 min, 40 min, 45 min, 50 min, 55 min, 60 min, 1 h, 2 h, 3 h, 4 h, 5 h, 6 h, 7 h, 8 h, 9 h, 10 h, 11 h, 12 h, 13 h, 14 h, 15 h, and 16 h.

In some embodiments, duration of the second incubation is ≥30 s.

In some embodiments, the duration of the second incubation ranges from 5 min to 16 h, and specifically may be any one or within a range between any two of 5 min, 10 min, 15 min, 20 min, 25 min, 30 min, 35 min, 40 min, 45 min, 50 min, 55 min, 60 min, 1 h, 2 h, 3 h, 4 h, 5 h, 6 h, 7 h, 8 h, 9 h, 10 h, 11 h, 12 h, 13 h, 14 h, 15 h, and 16 h.

In another aspect, embodiments of the present disclosure provide a method for synthesizing a nucleotide strand of interest, including: performing a ligation reaction on a nicked double-stranded nucleic acid molecule and/or one or more nucleic acid substrates capable of forming the nicked double-stranded nucleic acid molecule, where during the ligation reaction, the procedure of high-temperature denaturation-low-temperature annealing according to any one of the preceding embodiments is performed for at least one time.

In some embodiments, the synthesizing method includes performing the procedure of high-temperature denaturation-low-temperature annealing for two or more times.

In some embodiments, the two or more times specifically include ≥2, 3, 4, 5, 6, 7, 8, 9, and 10 times.

The process of high-temperature denaturation-low-temperature annealing can eliminate nicked non-target double-stranded nucleic acid molecules or double-stranded nucleic acid molecule with "gaps" caused by mismatching, thereby improving the ligation efficiency and reducing the formation of ligation byproducts. In addition, since double-stranded structures are damaged by high temperature, direct reaction at high temperature may cause decreased ligation efficiency; therefore, by initially raising the temperature to denature nonspecific double-stranded nucleic acid, followed by annealing to a slightly low temperature, more nicked double-stranded molecules of interest can be formed and the nicks can be sealed, thus improving the ligation efficiency, and reducing the production of byproducts.

In some embodiments, the nicked double-stranded nucleic acid molecule includes any one or more of nicked RNA duplexes and nicked DNA/RNA hybrid duplexes.

In some embodiments, in the nicked double-stranded nucleic acid molecule, the term "nicked" may mean that at least one strand of the double-stranded nucleic acid molecule has at least one nick, that is, one strand may be nicked, or both strands may be nicked.

Specifically, the nicked DNA/RNA hybrid duplexes include at least one deoxyribonucleotide, and at least one nick has at least one end (3'-hydroxyl group and/or 5'-phosphate group) contains RNA.

In some embodiments, the nicked double-stranded nucleic acid molecule comprises linear and/or circular nucleic acid molecule.

In some embodiments, the nicked double-stranded nucleic acid molecule comprises natural and/or modified nucleic acid molecule.

In some embodiments, the nicked double-stranded nucleic acid molecule includes a nucleic acid substrate or is formed by mixing a nucleic acid substrate or mixing and annealing a nucleic acid substrate.

In some embodiments, the nicked double-stranded nucleic acid molecule includes a double-strand nucleic acid substrate with nick or is formed by mixing a nucleic acid substrate or mixing and annealing a nucleic acid substrate.

In some embodiments, the nucleic acid substrate includes any one or more of the following: natural and/or modified RNA single strands, natural and/or modified RNA duplexes, natural and/or modified DNA single strands, natural and/or modified DNA/RNA hybrid single strands and natural and/or modified DNA/RNA hybrid duplexes.

In some embodiments, in the nucleic acid substrate, the RNA single strands include linear RNA single strands and/or circular RNA single strands, the RNA duplexes include linear RNA duplexes and/or circular RNA duplexes, the DNA single strands include linear DNA single strands and/or circular DNA single strands, the DNA/RNA hybrid single strands include linear DNA/RNA hybrid single strands and/or circular DNA/RNA hybrid single strands, and the DNA/RNA hybrid duplexes include linear DNA/RNA hybrid duplexes and/or circular DNA/RNA hybrid duplexes.

In some embodiments, the RNA single strands include any one or more of mRNA, antisense oligonucleotides, siRNA, sgRNA, lncRNA, CircRNA and miRNA.

When the nucleic acid substrate is double-stranded and nicked, the nucleic acid substrate itself is a nicked double-stranded nucleic acid molecule. When the nucleic acid substrate is single-stranded, the nicked double-stranded nucleic acid molecule can be formed by mixing the nucleic acid substrate directly or by an additional annealing process after mixing the nucleic acid substrates.

In some embodiments, the nucleic acid substrate is annealed at a temperature ranging from 0° C. to 100° C., which specifically may be any one or within a range between any two of 0, 5, 10, 15, 20, 25, 30, 35, 40, 45, 50, 55, 60, 65, 70, 75, 80, 85, 90, 95, and 100° C.

In some embodiments, the process of forming the nicked double-stranded nucleic acid molecule with the nucleic acid substrate may occur in the process of mixing the nucleic acid substrate, without a separate heated annealing process, during which the nucleic acid substrate, enzyme, ATP, Mg2 and other essential molecules and solutions for the reaction aremixed directly and then start the ligation reaction, and the nucleic acid substrate specifically binds during the mixing, so as to form the nicked double-stranded nucleic acid molecule.

In some embodiments, the nucleic acid substrate has a fragment length of ≥2 nt.

In some embodiments, the fragment length of the nucleic acid substrate ranges from 2 nt to 200 nt, and specifically may be any one or within a range between any two of 2, 5, 7, 10, 13, 15, 17, 20, 23, 25, 27, 30, 33, 35, 37, 40, 43, 45, 47, 50, 53, 55, 57, 60, 63, 62, 67, 70, 73, 75, 77, 80, 85, 90, 100, 110, 120, 130, 140, 150, 160, 170, 180, 190, and 200 nt.

In some embodiments, the number of nucleic acid substrates is ≥1. When the nucleic acid substrate is a circular nicked double-stranded nucleic acid molecule, the number of nucleic acid substrates may be 1.

In some embodiments, the number of nucleic acid substrates is 1-50, and specifically may be any one or within a range between any two of 1, 2, 4, 6, 8, 10, 12, 14, 16, 18, 20, 22, 24, 26, 28, 30, 32, 34, 36, 38, 40, 42, 44, 46, 48, and 50.

The method in the present disclosure has no particular limitation on types of modifications, and all modification types are applicable. In some embodiments, the modification includes modification for enhancing stability and/or reducing innate immune response.

In some embodiments, the modification includes any one of modification of phosphate group, modification of base, modification of sugar ring and modification of glycosidic bond.

In some embodiments, the modification of phosphate group includes any one or more of the following: 5'-(E)-vinylphosphonate modification (5'-VP), phosphorothioate modification, phosphotriester modification, 5'-methylphosphonate modification, 5'-morpholino modification, phosphorodithioate modification, methoxypropyl phosphonate modification, S-5'-C-methyl analogue modification, short-chain alkyl or cycloalkyl intersugar bond modification, short-chain heteroatom or heterocyclic intersugar bond modification, or complete substitution of phosphate group with any one of amide, aminoxy, alkoxy and triazolyl.

In some embodiments, the modification of base includes any one or more of the following: 2,4-difluorotolylribonucleoside substitution, pseudouridine modification, 2-thiouridine modification, N1-methyl pseudouridine modification, 5-methyl uridine modification, 5-methoxyuridine modification, N6-methyl adenosine modification, N6,N6-dimethyladenosine modification, 3-methyluridine modification, N7-methylguanosine modification, 2,7-dimethylguanosine modification, 2,2,7-trimethylguanosine modification, 5-methylcytidine modification, 5-hydroxymethylcytosine modification, 5-bromo-uracil modification, 5-iodo-uracil modification, propynyluracil nucleoside modification, N-ethylpiperidine-6-triazole modified adenosine modification, 6'-phenylpyrrolocytosine modification, 2-aminopurine modification, inosine modification, 2,6-diaminopurine modification, 2-pyrimidone modification and 5-methylcytosine modification.

In some embodiments, the modification of sugar ring includes any one or more of the following: 2'-methoxy modification, 2'-deoxy-2'-fluoro modification, 2'-O-methoxyethyl modification, Locked Nucleic Acid (LNA) modification, Unlocked Nucleic Acid (UNA) modification, Bridged Nucleic Acid (BNA) modification, Tricyclo-DNA (tcDNA) modification, Phosphorodiamidate Morpholino Oligomer (PMO) modification, 2'-deoxynucleotide modification, (S)-constrained ethyl bicyclic nucleic acid modification, peptide nucleic acid modification and glycomimetic modification.

In some embodiments, the glycomimetic includes one or more of the following: cyclobutyl in cyclobutyl nucleoside for replacing pentofuranosyl group, morpholinyl in morpholino nucleic acid (MNA), peptide backbone in peptide nucleic acid (PNA), polyethylene glycol backbone in glycol nucleic acid (GNA), threitol backbone in threose nucleic acid (TNA) and butyl backbone in acyclic butyl nucleic acid (BuNA).

In some embodiments, the modification of glycosidic bond includes replacement of C—N bond in glycosidic linkage with any one of C-C, C—O and C-S.

In some embodiments, the nucleotide strand of interest has a sequence length ≥2 nt, 10 nt, 20 nt or 50 nt.

In some embodiments, the sequence length of the nucleotide strand of interest may range from 10 nt to 200 nt, and specifically may be any one or within a range between any two of 10, 20, 30, 40, 50, 60, 70, 80, 90, 100, 120, 140, 160, 180, and 200 nt.

In some embodiments, the nucleotide strand of interest comprises linear and/or circular nucleotide strand.

In some embodiments, the nucleotide strand of interest is any one or more of RNA single strand, RNA duplex, DNA/RNA hybrid single strand and DNA/RNA hybrid duplex.

In some embodiments, the synthesizing method further includes isolating and purifying the ligated product, so as to obtain the nucleotide strand of interest.

In some embodiments, the synthesizing method further includes adding a ligase during the ligation reaction, where the ligase seals the nick by a phosphodiester bond.

In some embodiments, the ligase includes RNA ligases for ligating duplex.

In some embodiments, the ligases include RNA ligases of Rnl2 family and Rn15 family.

In some embodiments, the ligases include: thermostable RNA ligases for ligating duplex. The thermostable ligases are ligases with high stability at a set temperature during ligation.

In some embodiments, the ligases include wild-type T4 RNA ligase 2 or mutants thereof.

In some embodiments, the amino acid sequence of the wild-type T4 RNA ligase 2 has at least 80% identity to a sequence as set forth in SEQ ID NO: 1 or 2. In some embodiments, "having at least 80% identity" specifically refers to having the identity of any one or within a range between any two of 80%, 82%, 84%, 86%, 88%, 90%, 92%, 94%, 96%, 98%, and 100%.

In some embodiments, the mutants have mutation at any one or more sites of positions 62, 103, 166, 168, 193, 217, 260, 297, 298, 303, 306, 311, 313 and 318 of the amino acid sequence of the wild-type T4 RNA ligase 2. Having the mutation means that substitution or deletion of an amino acid residue occurs at corresponding site.

In some embodiments, the mutation at position 62 includes A62W; the mutation at position 103 includes P103G; the mutation at position 166 includes N166P; the mutation at position 168 includes L168F; the mutation at position 193 includes N193K, meaning that N at position 193 of the amino acid sequence is substituted with K; the mutation at position 217 includes any one of R217A, R217Q, R217N and R217P; the mutation at position 260 includes C260D; the mutation at position 297 includes T297A; the mutation at position 298 includes S298E; the mutation at position 303 includes T303D; the mutation at position 306 includes any one of Q306A, Q306D and Q306E; the mutation at position 311 includes any one of S311E, S311D, S311A and S311V; and the mutation at position 313 includes I313V.

In some embodiments, the mutants have any one or a combination of following mutations relative to the wild-type T4 RNA ligase 2: A62W, P103G, N166P, L168F, R217P, R217A, R217N, R217Q and C260D.

In some embodiments, the mutants have any one or a combination of following mutation combinations relative to the wild-type T4 RNA ligase 2: N193K-S311D, N193K-R217P, N193K-T303D, N193K-T297A, T297A-Q306D, N193K-I313V, R217P-S298E, R217P-T297A, R217P-I313V, and S311E-I313V.

In some embodiments, the mutants have any one or a combination of following mutation combinations relative to the wild-type T4 RNA ligase 2: R217P-T297A-S311E, R217P-S298E-S311D, R217P-T297A-I313V, N193K-R217P-C260D, R217P-S311E-I313V, R217P-T303D-I313V, N193K-R217P-T303D-S311E, N193K-R217P-T303D-I313V, N193K-R217P-T303D-V318T, N193K-R217P-S311E-I313V, N193K-R217P-T303D-S311E-I313V, A62W-N193K-R217P-T303D-S311E-I313V, P103G-N193K-R217P-T303D-S311E-I313V, N166P-N193K-R217P-T303D-S311E-I313V, L168F-N193K-R217P-T303D-S311E-I313V, N193K-R217P-C260D-T303D-S311E-I313V-V318T, L168F-N193K-R217P-C260D-S311E-T303D-I313V-V318T, A62W-L168F-N193K-R217P-C260D-T303D-S311E-I313V-V318T, P103G-L168F-N193K-R217P-C260D-T303D-S311E-I313V-V318T, A62W-P103G-L168F-N193K-R217P-C260D-T303D-S311E-I313V-V318T, A62W-P103G-N166P-L168F-N193K-R217P-C260D-T303D-S311E-I313V-V318T, A62W-N166P-L168F-N193K-R217P-C260D-T303D-S311E-I313V-V318T, P103G-N166P-L168F-N193K-R217P-C260D-T303D-S311E-I313V-V318T and N166P-L168F-N193K-R217P-C260D-T303D-S311E-I313V-V318T.

In some embodiments, reaction duration of the synthesizing method is ≥5 min. In some embodiments, the reaction duration may range from 5 min to 16 h, and specifically may be any one or within a range between any two of 5 min, 30 min, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5 and 16 h.

In some embodiments, a system of the synthesis reaction includes: a nucleic acid substrate, enzyme, ATP and Mg2.

In another aspect, embodiments of the present disclosure further provide a kit, including a reagent for implementing the synthesizing method according to any one of the preceding embodiments.

In another aspect, embodiments of the present disclosure further provide use of a target reagent in preparation of a product for synthesizing nucleotide strands, where the target reagent is a reagent for implementing the synthesizing method according to any one of the preceding embodiments.

In some embodiments, the reagent for implementing the synthesizing method according to any one of the preceding embodiments includes the thermostable ligase according to any one of the preceding embodiments and a reaction solution for synthesizing nucleotide strands.

In some embodiments, the reaction solution for synthesizing nucleotide strands includes any one or more of 40-60 mM Tris-HCl (pH 7.8-8.2), 10-14 mM MgCl2, 0.1-5 mM DTT, and 1-10 mM ATP. Each concentration is an action concentration of each component in the reaction system.

Specifically, the action concentration of Tris-HCl may be any one or within a range between any two of 40, 42, 44, 46, 48, 50, 52, 54, 56, 58, and 60 mM. The action concentration of MgCl2 may be any one or within a range between any two of 10, 11, 11.5, 12, 12.5, 13, and 14 mM. The action concentration of DTT may be any one or within a range between any two of 0.1, 0.5, 1, 1.5, 2, 2.5, 3, 3.5, 4, 4.5, and 5 mM. The action concentration of ATP may be any one or within a range between any two of 1, 1.5, 2, 2.5, 3, 3.5, 4, 4.5, 5, 6, 7, 8, 9, and 10 mM.

In some embodiments, the ligase at a final concentration ranging from 0.03 µM to 30 µM is added per 0.5-30 mM of the nucleic acid substrate. The 0.5-30 mM specifically may be any one or within a range between any two of 0.5, 1, 1.5, 1.6, 1.8, 2, 2.5, 3, 3.5, 4, 4.5, 5, 10, 15, 20, 25, and 30 mM. The 0.03-30 µM specifically may be any one or within a range between any two of 0.03, 0.04, 0.05, 0.1, 0.15, 0.2, 0.3, 0.4, 0.5, 0.6, 0.7, 0.8, 0.9, 1, 2, 3, 4, 5, 6, 7, 8, 9, 10, 15, 20, 25, and 30 µM.

Characteristics and performances of the present disclosure are further described in detail below in conjunction with examples.

Example 1

A method for synthesizing nucleotide strands was provided, including:

20 µL of reaction solution containing various oligonucleotides (nucleic acid substrates) at a final concentration of 1.6

Example 3

A method for synthesizing nucleotide strands was provided, which was substantially the same as the synthesizing method provided in Example 1, except that the set temperature was 42° C.

Example 4

A method for synthesizing nucleotide strands was provided, which was substantially the same as the synthesizing method provided in Example 1, except that the set temperature was 37° C.

Example 5: Synthesis of Nucleotide Strands was Achieved Through Reaction at High Temperatures, with Reduced Production of Byproducts 4 fragments of oligonucleotides in Table 1 were used as nucleic acid substrates. Based on the synthesizing method provided in Examples 1-4, the 4 fragments of oligonucleotides were ligated as shown in FIG. 1, with the wild-type T4 Rnl2 (amino acid sequence as forth in SEQ ID NO: 2) and its mutants Mut3, Mut6 and Mut9 as thermostable ligases.

Mut3 had mutation N193K-R217P-C260D on the basis of SEQ ID NO: 2.

Mut6 had mutation N193K-R217P-S311E-I313V on the basis of SEQ ID NO: 2.

Mut9 had mutation L168F-N193K-R217P-T303D-S311E-I313V on the basis of SEQ ID NO: 2.

For convenience, oligonucleotide generated from ligation reaction of F1 and F2 is designated as sense strand (abbreviated as SS), and oligonucleotide generated from F3 and F4 is designated as antisense strand (abbreviated as AS).

TABLE 1

| Oligonucleotides Used in Ligation Reaction in Examples 1-5 | | | |
|---|---|---|---|
| Fragment | Name | Sequence | SEQ ID NO: |
| SS strand 5' end | F1 | Pho-A-C-G-C-A-U-G-A | 3 |
| SS strand 3' end | F2 | Pho-A-C-U-G-C-U-A-C-U-U-A-U-C-A | 4 |
| AS strand 5' end | F3 | U-G-A-U-A-A-G-U-A-G-C | 5 |
| AS strand 3' end | F4 | Pho-A-G-U-U-C-A-U-G-C-G-U | 6 | mM for each, 50 mM Tris-HCl (pH 8.0), 12 mM MgCl2, 1 mM DTT, 4 mM ATP and 0.005 mg/mL of ligase was added into a 200 µL microtube, and subjected to ligation reaction at set temperature maintained by a PCR thermocycler. 2 h after initiation of the reaction, 1 µL of the reaction solution was sampled and 49 µL of a 10 mM EDTA solution was added to terminate the reaction.

In the above, the set temperature was 45° C.

Example 2

A method for synthesizing nucleotide strands was provided, which was substantially the same as the synthesizing method provided in Example 1, except that the set temperature was 50° C.

Note: "Pho" represents the phosphate group at the 5' end; and "-" represents phosphodiester bond. Sequences as set forth in SEQ ID NOs: 3-6 are unmodified sequences.

After the reaction, the product was separated using HPLC, and components of each peak were analyzed using mass spectrometry. A proportion of the product was calculated by dividing peak areas of various products in HPLC chromatogram by a total peak area of nucleotides in a whole chromatogram, that is:

$$\text{Product proportion} = \frac{\text{Area (target product or byproduct)}}{\text{Area } (F1-4+AS+SS+\text{byproduct})}.$$

Results of the example are listed in Table 2.

TABLE 2

| | | Target Product | Byproduct | | | | | |
|---|---|---|---|---|---|---|---|---|
| Variant | Reaction Temperature | AS + SS (%) | F2 + F3 | F1 + F3 + F4 | F1 + F2 + F3 | F1 + F1 + F2 | F1 + F2 + F3 + F4 | Total Byproduct |
| T4 | 37° C. | 62.4% | 8.0% | 3.2% | 1.7% | 0.6% | 0.1% | 13.6% |
| Rnl2 | 42° C. | 55.6% | 2.5% | 1.9% | 1.7% | 0.2% | 0.1% | 6.4% |
| | 45° C. | 25.4% | 0.8% | 1.5% | 0.5% | ND | ND | 2.8% |
| | 50° C. | 10.8% | ND | ND | ND | ND | ND | ND |
| Mut3 | 42° C. | 70.2% | 2.0% | 2.0% | 1.5% | 0.1% | ND | 5.6% |
| | 45° C. | 88.9% | 0.8% | 0.1% | 1.0% | ND | ND | 1.9% |
| | 50° C. | 90.2% | ND | ND | ND | ND | ND | ND |
| Mut6 | 42° C. | 75.1% | 1.8% | 1.5% | 1.5% | 0.1% | 0.5% | 5.4% |
| | 45° C. | 88.2% | 0.8% | 1.0% | 0.8% | ND | ND | 2.6% |
| | 50° C. | 90.0% | ND | ND | ND | ND | ND | ND |
| Mut9 | 42° C. | 70.8% | 2.1% | 1.4% | 1.3% | 0.1% | 0.3% | 5.2% |
| | 45° C. | 89.5% | 1.0% | 0.8% | 0.5% | ND | ND | 2.3% |
| | 50° C. | 91.6% | ND | ND | ND | ND | ND | ND |

Note: "ND" indicates that corresponding product was not detected in liquid phase or mass spectrometry analysis.

In this example, after 2 h of the reaction at 37° C., the yield of the target product of the wild-type T4 Rnl2 was 62.4%, and 13.6% of non-target byproducts were produced, whereas when the reaction temperature was raised to 42° C., the yield of the target product was slightly decreased, but the byproducts were decreased by about 50%, indicating that raising the reaction temperature can indeed reduce the production of byproducts. When the reaction temperature was further raised to 45° C. and 50° C., the production of byproducts was further reduced. When the reaction temperature was raised to 50° C., no byproduct was produced, but the yield of the target product was only 10.8% at this time because the wild-type T4 Rnl2 was substantially deactivated at high temperatures. Whereas after 2 h of reaction of Mut3, Mut6 and Mut9 at 45° C., the yields of the target product were 88.9%, 88.2% and 89.5%, respectively, and the yields of byproducts were 1.9%, 2.6% and 2.3%, respectively. When Mut3, Mut6 and Mut9 were used to react at 50° C. for 2 h, the yields of the target product were 90.2%, 90.0% and 91.6%, and no byproduct was detected in liquid chromatography-mass spectrometry. The results of this example demonstrate that using the thermostable mutants of the present disclosure to react at high temperatures can significantly reduce the byproducts caused by base mismatching. Moreover, in this example, the yields of the target product of the reaction under high-temperature conditions were significantly higher than that at 37° C.

Example 6: Non-Natural Nucleic Acid Substrates were Ligated at High Temperatures, with Reduced Production of Byproducts Based on the method for synthesizing nucleic acid strands provided in Examples 1-4, the present example used the 4 fragments of oligonucleotides in Table 1 as nucleic acid substrates, and Mut3, Mut6 and Mut9 (the same as in Example 5) as ligases for ligation, with a schematic diagram of ligation of the nucleic acid substrates as shown in FIG. 2. Purified wild-type T4 Rn12 (SEQ ID NO: 2) was used as a control group to react under the same conditions.

The ribonucleotides as nucleic acid substrates in the present example were all non-natural ribonucleotides, including several common non-natural ribonucleotides in RNA therapeutic design: 2'-methoxy modification (2'—OCH3) at pentose 2'-position, 2'-deoxy-2'-fluoro (2'-F), 5'-(E)-vinylphosphonate modification of pentose 5'-position, thiophosphate modification at a-position phosphate and deoxyribonucleotides incorporated at specific sites. For descriptive convenience, oligonucleotide generated through ligation reaction of F1 and F2 is designated as sense strand (abbreviated as SS), and oligonucleotide generated from F3 and F4 is designated as antisense strand (abbreviated as AS).

TABLE 3

| | | | SEQ ID |
|---|---|---|---|
| Fragment | Name | Sequence | NO: |
| SS strand 5' end | F1 | VP-mA-fC-mG-fC-mA-dT-fG-mA | 7 |
| SS strand 3' end | F2 | Pho-msA-fC-mU-msG-fC-mU-fsA-mC-fU-mU-mA-fU-msC-fA | 8 |
| AS strand 5' end | F3 | mU-fG-mfA-mfU-mA-fA-mG-dU-mA-fG-mC | 9 |
| AS strand 3' end | F4 | Pho-msA-fG-mU-fU-mC-fA-mU-fG-mC-mG-mU | 10 |

_Oligonucleotides Used in Ligation Reaction in Example 6_

Note: "Pho" represents the phosphate group at the 5' end; "-" represents phosphodiester bond; "m" represents 2'-methoxy modification (2'—OCH3); "f" represents 2'-deoxy-2'-fluoro (2'-F) modification; "s" represents thiophosphate modification of a-phosphate; "d" represents that the nucleotide used is deoxyribonucleotide; "VP" represents 5'-(E)-vinylphosphonate modification (5'-VP); and sequences as set forth in SEQ ID NOs: 7-10 are unmodified sequences.

Detection and analysis methods of the nucleotide strands were the same as described in Example 5. Results are listed in Table 12.

TABLE 4

| | | Target Product | Byproduct | | | | | |
| --- | --- | --- | --- | --- | --- | --- | --- | --- |
| Variant | Reaction Temperature | AS + SS (%) | F2 + F3 | F1 + F3 + F4 | F1 + F2 + F3 | F1 + F1 + F2 | F1 + F2 + F3 + F4 | Total Byproduct |
| T4 Rnl2 | 37° C. | 65.4% | 8.5% | 4.1% | 1.5% | 0.6% | 0.2% | 14.9% |
| | 42° C. | 53.3% | 2.0% | 2.0% | 1.5% | 0.1% | 0.2% | 5.8% |
| | 45° C. | 26.5% | 1.0% | 1.2% | 0.3% | ND | ND | 2.5% |
| | 50° C. | 11.0% | ND | ND | ND | ND | ND | ND |
| Mut3 | 42° C. | 72.2% | 1.8% | 1.8% | 1.5% | 0.1% | ND | 5.2% |
| | 45° C. | 89.5% | 0.7% | 0.2% | 0.8% | ND | ND | 1.7% |
| | 50° C. | 89.2% | ND | ND | ND | ND | ND | ND |
| Mut6 | 42° C. | 78.1% | 1.5% | 1.3% | 1.8% | 0.1% | 0.8% | 5.5% |
| | 45° C. | 90.2% | 0.5 | 0.8 | 0.6 | ND | 0.2 | 2.1% |
| | 50° C. | 88.6% | ND | ND | ND | ND | ND | ND |
| Mut9 | 42° C. | 75.6% | 1.2% | 1.3% | 1.6% | 0.2% | 0.4% | 4.7% |
| | 45° C. | 88.2% | 0.5% | 0.5% | 0.9% | ND | 0.1% | 2.0% |
| | 50° C. | 90.1% | ND | ND | ND | ND | ND | ND |

Generation of Products in Ligation Reaction in Example 6

Note: "ND" indicates that corresponding product was not detected in liquid phase or mass spectrometry analysis.

In this example, after 2 h of the reaction at 37° C., the yield of the target product of the wild-type T4 Rnl2 was 65.4%, and at the same time 14.9% of non-target byproducts were produced, whereas when the reaction temperature was raised to 42° C., the yield of the target product was slightly decreased, but the byproducts were decreased by about 60%. When the reaction temperature was further raised to 45° C. and 50° C., the production of byproducts was further reduced. When the reaction temperature was raised to 50° C., no byproduct production was observed, but the yield of the target product was only 11% at this time because the wild-type T4 Rnl2 was substantially deactivated at high temperatures. Whereas after 2 h of reaction of Mut3, Mut6 and Mut9 at 45° C., the yields of the target product were 89.5%, 90.2% and 88.2%, respectively, and the yields of byproducts were 1.7%, 2.1% and 2.0%, respectively. When Mut3, Mut6 and Mut9 were used to react at 50° C. for 2 h, the yields were 89.2%, 90.2% and 90.1%, and no byproduct was detected in liquid chromatography-mass spectrometry. The results of this example demonstrate that using the thermostable mutants of the present disclosure to react at high temperatures can significantly reduce the byproducts caused by base mismatching, and this effect was not limited to ribonucleotide strands composed of natural ribonucleotides, it was applicable to ribonucleotide strands composed of non-natural ribonucleotides.

Example 7: Efficiency of Nucleotide Synthesis was Improved by Adding a Procedure of "High-Temperature Denaturation-Low-Temperature Annealing", with Reduced Production of Byproducts 20 μl of reaction solution containing various oligonucleotides (nucleic acid substrates) at a final concentration of 1.6 mM listed in Table 5, 50 mM Tris-HCl (pH 8.0), 12 mM MgCl2, 1 mM DTT, 4 mM ATP and 0.005 mg/ml of ligase was added into a 200 μl microtube, and subjected to reaction as shown in FIG. 3, at temperature regulated by a PCR thermocycler. The ligase included wild-type T4 Rnl2, thermostable ligases L168F-N193K-R217P-T303D-S311E-1313V (Mut9) and A62W-P103G-N166P-L168F-N193K-R217P-T303D-S311E-1313V (Mut23). In the above, Mut23 had mutation A62W-P103G-N166P-L168F-N193K-R217P-T303D-S311E-1313V on the basis of SEQ ID NO: 2.

The present example included several following experimental groups: Experimental Groups 1, 6 and 11, subjected to direct incubation at 37° C. for 4 h; Experimental Groups 2, 7 and 12, subjected to direct incubation at 45° C. for 4 h, Experimental Groups 3, 8 and 13, subjected to direct incubation at 55° C. for 4 h; Experimental Groups 4, 9 and 14, subjected to incubation at 45° C. for 1 h, followed by heating to 55° C. and incubation for 1 h, and cooling to 45° C. for annealing and incubation for 2 h; Experimental Groups 5, 10 and 15, first subjected to incubation at 55° C. for 1 h, followed by cooling to 45° C. for annealing and incubation for 1 h, subsequently heating to 55° C. and incubation for 1 h, and then cooling to 45° C. for annealing and incubation for 1 h. After the reaction was finished, 1 μL of the reaction solution was sampled and 49 μL of a 10 mM EDTA solution was added to terminate the reaction. Reaction products were analyzed by liquid chromatography-mass spectrometry.

TABLE 5

Oligonucleotides Used in Example 7

| Fragment | Name | Sequence | SEQ ID NO: |
|---|---|---|---|
| SS strand 5' end | F1 | VP-mA-mG-mC-mC-msU-fU-mA-mA | 11 |
| SS strand 3' end | F2 | PO$_4$-mA-mU-mA-fC-fA-fA-mU-mA-mU-mU-mA-mA-mG-mC-mG-mA | 12 |
| AS strand 5' end | F3 | mU-mC-mG-mC-mU-fU-msA-msA-msU-mA-mU-mU-mG | 13 |
| AS strand 3' end | F4 | PO$_4$-fU-mA-mU-mU-fU-mA-mA-mG-mG-mC-msU | 14 |

Note: "Pho" represents the phosphate group at the 5' end; "-" represents phosphodiester bond; "m" represents 2'-methoxy modification (2'—OCH3); "f" represents 2'-deoxy-2'-fluoro (2'-F) modification; "s" represents thio modification of a-phosphate; "d" represents the nucleotide used being deoxyribonucleotide; and "VP" represents 5'-(E)-vinylphosphonate modification (5'-VP).

The detection and analysis methods were the same as those described in Example 5, and results are listed in Table 6.

TABLE 6

Generation of Products in Ligation Reaction in Example 7

| Variant | Reaction Group | Target Product SS + AS (%) | F2 + F3 (%) | Byproduct F1 + F2 + F3 (%) | F1 + F2 + F3 + F4 (%) | Total Byproduct (%) |
|---|---|---|---|---|---|---|
| T4 Rnl2 | Experimental Group 1 | 45.2 | 7.6 | 3.0 | 1.5 | 12.1 |
| | Experimental Group 2 | 45.9 | 2.5 | 1.0 | 0.8 | 5.3 |
| | Experimental Group 3 | 6.8 | ND | ND | ND | ND |
| | Experimental Group 4 | 38.0 | 1.8 | 0.8 | 0.4 | 3.0 |
| | Experimental Group 5 | ND | ND | ND | ND | ND |
| Mut9 | Experimental Group 6 | 43.4 | 8.0 | 2.7 | 1.0 | 11.7 |
| | Experimental Group 7 | 68.2 | 2.8 | 1.5 | 0.7 | 5.0 |
| | Experimental Group 8 | 46.8 | ND | ND | ND | ND |
| | Experimental Group 9 | 89.7 | 1.2 | 0.5 | 0.3 | 2.0 |
| | Experimental Group 10 | 91.1 | ND | ND | ND | ND |
| Mut23 | Experimental Group 11 | 50.5 | 8.2 | 2.9 | 1.3 | 12.4 |
| | Experimental Group 12 | 75.5 | 3.0 | 1.8 | 1.0 | 5.8 |
| | Experimental Group 13 | 52.6 | ND | ND | ND | ND |
| | Experimental Group 14 | 92.2 | 1.0 | 0.4 | 0.1 | 1.5 |

TABLE 6-continued

Generation of Products in Ligation Reaction in Example 7

| Variant | Reaction Group | Target Product SS + AS (%) | F2 + F3 (%) | Byproduct F1 + F2 + F3 (%) | F1 + F2 + F3 + F4 (%) | Total Byproduct (%) |
|---|---|---|---|---|---|---|
| | Experimental Group 15 | 93.5 | ND | ND | ND | ND |

Note: "ND" indicates that corresponding product was not detected in liquid phase or mass spectrometry analysis.

The results of the example demonstrate that after Mut9 was used to react under a condition of 55° C. for 4 h (Experimental Group 3), the yield of 46.8% was obtained, and no detectable byproduct was produced, while when the wild-type T4 Rnl2 was used to react under the condition of 55° C. for 4 h (Experimental Group 4), no detectable target product was produced. This result demonstrates that Mut9 had better thermal stability and that using Mut9 to react under the condition of 55° C. could effectively reduce the byproduct production. However, according to the results of the example, the byproducts produced after 4 h of reaction of Mut9 under the condition of 55° C. were significantly less than those after 4 h of reaction of Mut9 at 45° C., but the yield of Mut9 after 4 h of reaction under the condition of 55° C. (Experimental Group 8) was 46.8%, lower than 68.2% of Mut9 after 4 h of reaction at 45° C. When Mut9 was first incubated at 45° C. for 1 h, heated to 55° C. and incubated for 1 h, and then cooled to 45° C. for annealing and incubated for another 2 h (Experimental Group 9), the yield of the target product obtained was 89.7%, higher than the yield of 68.2% of Mut9 subjected to direct incubation at 45° C. for 4 h (Experimental Group 7), and the proportion of byproducts was much lower, only 2%. When Mut9 was first incubated at 55° C. for 1 h, then cooledto 45° C. for annealing and incubated for 1 h, subsequently heated to 55° C. and incubated for 1 h, and then cooled to 45° C. for annealing and incubated for 1 h, the yield obtained was 91.1% (Experimental Group 10), and no byproduct was detected. The experimental result of Mut23 in the present example was substantially consistent with that of Mut9. The above results demonstrate that when the thermostable T4 Rnl2 mutants are used for ligation, adding the step of "high-temperature denaturation-low-temperature annealing" can significantly elevate the yield of the target product while reducing the byproduct production.

Sequence information involved in the present disclosure is partially listed in table below.

| Sequence | SEQ ID NO: |
|---|---|
| MFKKYSSLENHYNSKFIEKLYSLGLTGGEWVAREKIHGTNFSLIIERDKVTCAKRT<br>GPILPAEDFFGYEIILKNYADSIKAVQDIMETSAVVSYQVFGEFAGPGIQKNVDYCD<br>KDFYVFDIIVTTESGDVTYVDDYMMESFCNTFKFKMAPLLGRGKFEELIKLPNDLD<br>SVVQDYNFTVDHAGLVDANKCVWNAEAKGEVFTAEGYVLKPCYPSWLRNGNR<br>VAIKCKNSKFSEKKKSDKPIKAKVELSEADNKLVGILACYVTLNRVNNVISKIGEIG<br>PKDFGKVMGLTVQDILEETSREGITLTQADNPSLIKKELVKMVQDVLRPAWIELVS | 1 |
| MFKKYSSLENHYNSKFIEKLYSLGLTGGEWVAREKIHGTNFSLIIERDKVTCAKRT<br>GPILPAEDFFGYEIILKNYADSIKAVQDIMETSAVVSYQVFGEFAGPGIQKNVDYGD<br>KDFYVFDIIVTTESGDVTYVDDYMMESFCNTFKFKMAPLLGRGKFEELIKLPNDLD<br>SVVQDYNFTVDHAGLVDANKCVWNAEAKGEVFTAEGYVLKPCYPSWLRNGNR<br>VAIKCKNSKFSEKKKSDKPIKAKVELSEADNKLVGILACYVTLNRVNNVISKIGEIG<br>PKDFGKVMGLTVQDILEETSREGITLTQADNPSLIKKELVKMVQDVLRPAWIELVS | 2 |

15

The above-mentioned are merely for preferred embodiments of the present disclosure, but are not intended to limit the present disclosure. For those skilled in the art, various modifications and changes could be made to the present disclosure. Any amendments, equivalent replacements, improvements and so on, made within the spirit and principle of the present disclosure, should be covered within the scope of protection of the present disclosure.

What is claimed is:

1. A method for synthesizing a nucleotide strand of interest, comprising: performing a ligation reaction on a nicked double-stranded nucleic acid molecule and/or a nucleic acid substrate capable of forming the nicked double-stranded nucleic acid molecule under a condition of a first set temperature, wherein the first set temperature is ≥42° C., wherein the nucleic acid substrate capable of forming the nicked double-stranded nucleic acid molecule is an oligonucleotide containing a 5'-monophosphate group and/or a 3'-hydroxyl group, and the nicked double-stranded nucleic acid molecule comprises any one or more of nicked RNA duplexes and nicked DNA/RNA hybrid duplexes.

2. The synthesizing method according to claim 1, wherein the first set temperature ranges from 42° C. to 60° C.;

optionally, reaction duration under the condition of the first set temperature is ≥30 s;

optionally, the reaction duration under the condition of the first set temperature ranges from 5 min to 16 h;

optionally, before, during and/or after the reaction under the condition of the first set temperature, the synthesizing method further comprises performing a procedure of high-temperature denaturation-low-temperature annealing for at least once, wherein the high-temperature denaturation comprises performing a first incubation at a second set temperature, the second set temperature ≥ the first set temperature; and the low-temperature annealing comprises performing a second incubation at a third set temperature, the third set temperature < the second set temperature;

optionally, the second set temperature ranges from 42° C. to 60° C.;

optionally, the third set temperature is ≥4° C.;

optionally, the synthesizing method further comprises: performing the procedure of high-temperature denaturation-low-temperature annealing for two or more times;

optionally, duration of the first incubation is ≥30 s optionally, the duration of the first incubation ranges from 5 min to 16 h;

optionally, duration of the second incubation is ≥30 s; and optionally, the duration of the second incubation ranges from 5 min to 16 h.

3. A method for synthesizing a nucleotide strand of interest, comprising: performing a ligation reaction on a nicked double-stranded nucleic acid molecule and/or a nucleic acid substrate capable of forming the nicked double-stranded nucleic acid molecule, wherein during the ligation reaction, the procedure of high-temperature denaturation-low-temperature annealing in the synthesizing method according to claim 2 is performed for at least once; and optionally, the synthesizing method comprises performing the procedure of high-temperature denaturation-low-temperature annealing for twice or more times.

4. The synthesizing method according to claim 1, wherein the synthesizing method further comprises adding a ligase during the ligation reaction;

optionally, the ligase comprises RNA ligases for ligating duplex;

optionally, the ligases comprise RNA ligases of Rnl2 family and Rnl5 family;

optionally, the ligases comprise: thermostable RNA ligases for ligating duplex;

optionally, the ligases comprise wild-type T4 RNA ligase 2 or mutants thereof;

optionally, the amino acid sequence of the wild-type T4 RNA ligase 2 has at least 80% identity to a sequence as set forth in SEQ ID NO: 1 or 2;

optionally, the mutants have mutation at any one or more sites of positions 62, 103, 166, 168, 193, 217, 260, 297, 298, 303, 306, 311, 313 and 318 of the amino acid sequence of the wild-type T4 RNA ligase 2;

optionally, the mutants have any one or a combination of following mutations relative to the wild-type T4 RNA ligase 2: A62W, PI03G, N166P, L168F, R217P, R217A, R217N, R217Q and C260D;

optionally, the mutants have any one or a combination of following mutation combinations relative to the wild-type T4 RNA ligase 2: N193K-S311D, N193K-R217P, N193K-T303D, N193K-T297A, T297A-Q306D, N193K-I313V, R217P-S298E, R217P-T297A, R217P-I313V, and S311E-I313V; and optionally, the mutants have any one or a combination of following mutation combinations relative to the wild-type T4 RNA ligase 2: R217P-T297A-S311E, R217P-S298E-S311D, R217P-T297A-I313V, N193K-R217P-C260D, R217P-S311E-I313V, R217P-T303D-I313V, N193K-R217P-T303D-S311E, N193K-R217P-T303D-I313V, N193K-R217P-T303D-V318T, N193K-R217P-S311E-I313V, N193K-R217P-T303D-S311E-I313V, A62W-N193K-R217P-T303D-S311E-I313V, P103G-N193K-R217P-T303D-S311E-I313V, N166P-N193K-R217P-T303D-S311E-I313V, L168F-N193K-R217P-T303D-S311E-I313V, N193K-R217P-C260D-T303D-S311E-I313V-V318T, L168F-N193K-R217P-C260D-S311E-T303D-I313V-V318T, A62W-L168F-N193K-R217P-C260D-T303D-S311E-I313V-V318T, P103G-L168F-N193K-R217P-C260D-T303D-S311E-I313V-V318T, A62W-P103G-L168F-N193K-R217P-C260D-T303D-S311E-I313V-V318T, A62W-P103G-N166P-L168F-N193K-R217P-C260D-T303D-S311E-I313V-V318T, A62W-N166P-L168F-N193K-R217P-C260D-T303D-S311E-I313V-V318T, P103G-N166P-L168F-N193K-R217P-C260D-T303D-S311E-I313V-V318T and N166P-L168F-N193K-R217P-C260D-T303D-S311E-I313V-V318T.

5. The synthesizing method according to claim 1, wherein the nicked double-stranded nucleic acid molecule comprises linear and/or circular nucleic acid molecule;

optionally, the nicked double-stranded nucleic acid molecule comprises a nucleic acid substrate or is formed by mixing the nucleic acid substrates;

optionally, the nucleic acid substrate comprises any one or more of the following: natural and/or modified RNA single strands, natural and/or modified RNA duplexes, natural and/or modified DNA single strands, natural and/or modified DNA/RNA hybrid single strands and natural and/or modified DNA/RNA hybrid duplexes;

optionally, in the nucleic acid substrate, the RNA single strands comprise linear RNA single strands and/or circular RNA single strands, the RNA duplexes comprise linear RNA duplexes and/or circular RNA duplexes, the DNA single strands comprise linear DNA single strands and/or circular DNA single strands, the DNA/RNA hybrid single strands comprise linear DNA/RNA hybrid single strands and/or circular DNA/RNA hybrid single strands, and the DNA/RNA hybrid duplexes comprise linear DNA/RNA hybrid duplexes and/or circular DNA/RNA hybrid duplexes;

optionally, the RNA single strands comprise any one or more of mRNA, antisense oligonucleotides, siRNA, sgRNA, lncRNA, CircRNA and miRNA;

optionally, the nucleic acid substrate has a fragment length of >2 nt; and optionally, the fragment length of the nucleic acid substrate ranges from 2 nt to 200 nt.

6. The synthesizing method according to claim 5, wherein the modification comprises modification for enhancing stability and/or reducing innate immune response; and optionally, the modification comprises any one of modification of phosphate group, modification of base, modification of sugar ring and modification of glycosidic bond.

7. The synthesizing method according to claim 6, wherein the modification of phosphate group comprises any one or more of the following: 5'-(E)-vinylphosphonate modification, phosphorothioate modification, phosphotriester modification, 5'-methylphosphonate modification, 5'-morpholino modification, phosphorodithioate modification, methoxypropyl phosphonate modification, S-5'-C-methyl analogue modification, short-chain alkyl or cycloalkyl intersugar bond modification, short-chain heteroatom or heterocyclic intersugar bond modification, or complete substitution of phosphate group with any one of amide, aminoxy, alkoxy and triazolyl;

optionally, the modification of base comprises any one or more of the following: 2,4-difluorotolylribonucleoside substitution, pseudouridine modification, 2-thiouridine modification, N1-methyl pseudouridine modification, 5-methyl uridine modification, 5-methoxyuridine modification, N6-methyl adenosine modification, N6,N6-dimethyladenosine modification, 3-methyluridine modification, N7-methylguanosine modification, 2,7-dimethylguanosine modification, 2,2,7-trimethylguanosine modification, 5-methylcytidine modification, 5-hydroxymethylcytosine modification, 5-bromouracil modification, 5-iodo-uracil modification, propynyluracil nucleoside modification, N-ethylpiperi-
dine-6-triazole modified adenosine modification,
6'-phenylpyrrolocytosine modification, 2-aminopurine
modification, inosine modification, 2,6-diaminopurine
modification, 2-pyrimidone modification and 5-meth-
ylcytosine modification;

optionally, the modification of sugar ring comprises any
one or more of the following: 2'-methoxy modification,
2'-deoxy-2'-fluoro modification, 2'-O-methoxyethyl
modification, locked nucleic acid modification,
unlocked nucleic acid modification, bridged nucleic
acid modification, tricyclo-DNA modification, phos-
phorodiamidate morpholino oligomer modification,
2'-deoxynucleotide modification, (S)-constrained ethyl
bicyclic nucleic acid modification, peptide nucleic acid
modification and glycomimetic modification;

optionally, the glycomimetic comprises any one or more
of the following: cyclobutyl in cyclobutyl nucleoside
for replacing pentofuranosyl group, morpholinyl in
morpholino nucleic acid, peptide backbone in peptide
nucleic acid, polyethylene glycol backbone in glycol
nucleic acid, threitol backbone in threose nucleic acid
and butyl backbone in acyclic butyl nucleic acid; and optionally, the modification of the glycosidic bond com-
prises replacement of C-N bond in glycosidic linkage
with any one of C-C, C—O and C-S.

8. The synthesizing method according to claim 1, wherein
the nucleotide strand of interest has a sequence length >2 nt;

optionally, the nucleotide strand of interest has the
sequence length >20 nt; and optionally, the nucleotide strand of interest has the
sequence length >50 nt.

9. The synthesizing method according to claim 1, wherein
reaction duration of the synthesizing method is ≥5 min optionally, the reaction duration of the synthesizing
method ranges from 5 min to 16 h; and optionally, the reaction duration of the synthesizing
method ranges from 1 h to 16 h.

10. The synthesizing method according to claim 1,
wherein the nucleotide strand of interest comprises linear
and/or circular nucleotide strand;

optionally, the nucleotide strand of interest is any one or
more of RNA single strand, RNA duplex, DNA/RNA
hybrid single strand and DNA/RNA hybrid duplex; and optionally, the synthesizing method further comprises
isolating and purifying a ligated product, so as to obtain
the nucleotide strand of interest.

11. The synthesizing method according to claim 2,
wherein the synthesizing method further comprises adding a
ligase during the ligation reaction;

optionally, the ligase comprises RNA ligases for ligating
duplex:

optionally, the ligases comprise RNA ligases of Rnl2
family and Rnl5 family;

optionally, the ligases comprise: thermostable RNA
ligases for ligating duplex;

optionally, the ligases comprise wild-type T4 RNA ligase
2 or mutants thereof;

optionally, the amino acid sequence of the wild-type T4
RNA ligase 2 has at least 80% identity to a sequence as
set forth in SEQ ID NO: 1 or 2;

optionally, the mutants have mutation at any one or more
sites of positions 62, 103, 166, 168, 193, 217, 260, 297,
298, 303, 306, 311, 313 and 318 of the amino acid
sequence of the wild-type T4 RNA ligase 2;

optionally, the mutants have any one or a combination of
following mutations relative to the wild-type T4 RNA ligase 2: A62W, PI03G, N166P, L168F, R217P, R217A,
R217N, R217Q and C260D;

optionally, the mutants have any one or a combination of
following mutation combinations relative to the wild-
type T4 RNA ligase 2: N193K-S311D, N193K-R217P,
N193K-T303D, N193K-T297A, T297A-Q306D,
N193K-1313V, R217P-S298E, R217P-T297A, R217P-
1313V, and S311E-1313V; and optionally, the mutants have any one or a combination of
following mutation combinations relative to the wild-
type T4 RNA ligase 2: R217P-T297A-S311E, R217P-
S298E-S311D, R217P-T297A-1313V, N193K-R217P-
C260D, R217P-S311E-1313V, R217P-T303D-1313V,
N193K-R217P-T303D-S311E, N193K-R217P-
T303D-1313V, N193K-R217P-T303D-V318T,
N193K-R217P-S311E-1313V, N193K-R217P-T303D-
S311E-1313V, A62W-N193K-R217P-T303D-S311E-
1313V, P103G-N193K-R217P-T303D-S311E-1313V,
N166P-N193K-R217P-T303D-S311E-1313V, L168F-
N193K-R217P-T303D-S311E-1313V, N193K-R217P-
C260D-T303D-S311E-1313V-V318T, L168F-N193K-
R217P-C260D-S311E-T303D-1313V-V318T, A62W-
L168F-N193K-R217P-C260D-T303D-S311E-1313V-
V318T, P103G-L168F-N193K-R217P-C260D-
T303D-S311E-1313V-V318T, A62W-P103G-L168F-
N193K-R217P-C260D-T303D-S311E-1313V-V318T,
A62W-P103G-N166P-L168F-N193K-R217P-C260D-
T303D-S311E-1313V-V318T, A62W-N166P-L168F-
N193K-R217P-C260D-T303D-S311E-1313V-V318T,
P103G-N166P-L168F-N193K-R217P-C260D-T303D-
S311E-1313V-V318T and N166P-L168F-N193K-
R217P-C260D-T303D-S311E-1313V-V318T.

12. The synthesizing method according to claim 3,
wherein the synthesizing method further comprises adding a
ligase during the ligation reaction;

optionally, the ligase comprises RNA ligases for ligating
duplex;

optionally, the ligases comprise RNA ligases of Rnl2
family and Rnl5 family;

optionally, the ligases comprise: thermostable RNA
ligases for ligating duplex;

optionally, the ligases comprise wild-type T4 RNA ligase
2 or mutants thereof;

optionally, the amino acid sequence of the wild-type T4
RNA ligase 2 has at least 80% identity to a sequence as
set forth in SEQ ID NO: 1 or 2;

optionally, the mutants have mutation at any one or more
sites of positions 62, 103, 166, 168, 193, 217, 260, 297,
298, 303, 306, 311, 313 and 318 of the amino acid
sequence of the wild-type T4 RNA ligase 2;

optionally, the mutants have any one or a combination of
following mutations relative to the wild-type T4 RNA
ligase 2: A62W, P103G, N166P, L168F, R217P,
R217A, R217N, R217Q and C260D;

optionally, the mutants have any one or a combination of
following mutation combinations relative to the wild-
type T4 RNA ligase 2: N193K-S31ID, N193K-R217P,
N193K-T303D, N193K-T297A, T297A-Q306D,
N193K-1313V, R217P-S298E, R217P-T297A, R217P-
1313V, and S311E-1313V; and optionally, the mutants have any one or a combination of
following mutation combinations relative to the wild-
type T4 RNA ligase 2: R217P-T297A-S311E, R217P-
S298E-S31ID, R217P-T297A-1313V, N193K-R217P-
C260D, R217P-S311E-1313V, R217P-T303D-1313V,
N193K-R217P-T303D-S31IE, N193K-R217P-T303D-
1313V, N193K-R217P-T303D-V318T, N193K-

R217P-S311E-1313V, N193K-R217P-T303D-S311E-1313V, A62W-N193K-R217P-T303D-S311E-1313V, P103G-N193K-R217P-T303D-S311E-1313V, N166P-N193K-R217P-T303D-S311E-1313V, L168F-N193K-R217P-T303D-S311E-1313V, N193K-R217P-C260D-T303D-S311E-1313V-V318T, L168F-N193K-R217P-C260D-S311E-T303D-1313V-V318T, A62W-L168F-N193K-R217P-C260D-T303D-S311E-1313V-V318T, P103G-L168F-N193K-R217P-C260D-T303D-S311E-1313V-V318T, A62W-P103G-L168F-N193K-R217P-C260D-T303D-S311E-1313V-V318T, A62W-P103G-N166P-L168F-N193K-R217P-C260D-T303D-S311E-1313V-V318T, A62W-N166P-L168F-N193K-R217P-C260D-T303D-S311E-1313V-V318T, P103G-N166P-L168F-N193K-R217P-C260D-T303D-S311E-1313V-V318T and N166P-L168F-N193K-R217P-C260D-T303D-S311E-1313V-V318T.

13. The synthesizing method according to claim 2, wherein the nicked double-stranded nucleic acid molecule comprises linear and/or circular nucleic acid molecule;

optionally, the nicked double-stranded nucleic acid molecule comprises a nucleic acid substrate or is formed by mixing the nucleic acid substrates;

optionally, the nucleic acid substrate comprises any one or more of the following: natural and/or modified RNA single strands, natural and/or modified RNA duplexes, natural and/or modified DNA single strands, natural and/or modified DNA/RNA hybrid single strands and natural and/or modified DNA/RNA hybrid duplexes;

optionally, in the nucleic acid substrate, the RNA single strands comprise linear RNA single strands and/or circular RNA single strands, the RNA duplexes comprise linear RNA duplexes and/or circular RNA duplexes, the DNA single strands comprise linear DNA single strands and/or circular DNA single strands, the DNA/RNA hybrid single strands comprise linear DNA/RNA hybrid single strands and/or circular DNA/RNA hybrid single strands, and the DNA/RNA hybrid duplexes comprise linear DNA/RNA hybrid duplexes and/or circular DNA/RNA hybrid duplexes;

optionally, the RNA single strands comprise any one or more of mRNA, antisense oligonucleotides, siRNA, sgRNA, lncRNA, CircRNA and miRNA;

optionally, the nucleic acid substrate has a fragment length of >2 nt; and optionally, the fragment length of the nucleic acid substrate ranges from 2 nt to 200 nt.

14. The synthesizing method according to claim 3, wherein the nicked double-stranded nucleic acid molecule comprises any one or more of nicked RNA duplexes and nicked DNA/RNA hybrid duplexes;

optionally, the nicked double-stranded nucleic acid molecule comprises linear and/or circular nucleic acid molecule;

optionally, the nicked double-stranded nucleic acid molecule comprises a nucleic acid substrate or is formed by mixing the nucleic acid substrates directly or mixing the nucleic acid substrates followed by an annealing process;

optionally, the nucleic acid substrate comprises any one or more of the following: natural and/or modified RNA single strands, natural and/or modified RNA duplexes, natural and/or modified DNA single strands, natural and/or modified DNA/RNA hybrid single strands and natural and/or modified DNA/RNA hybrid duplexes;

optionally, in the nucleic acid substrate, the RNA single strands comprise linear RNA single strands and/or circular RNA single strands, the RNA duplexes comprise linear RNA duplexes and/or circular RNA duplexes, the DNA single strands comprise linear DNA single strands and/or circular DNA single strands, the DNA/RNA hybrid single strands comprise linear DNA/RNA hybrid single strands and/or circular DNA/RNA hybrid single strands, and the DNA/RNA hybrid duplexes comprise linear DNA/RNA hybrid duplexes and/or circular DNA/RNA hybrid duplexes;

optionally, the RNA single strands comprise any one or more of mRNA, antisense oligonucleotides, siRNA, sgRNA, lncRNA, CircRNA and miRNA;

optionally, the nucleic acid substrate has a fragment length of >2 nt; and optionally, the fragment length of the nucleic acid substrate ranges from 2 nt to 200 nt.

15. The synthesizing method according to claim 2, wherein the nucleotide strand of interest has a sequence length ≥2 nt;

optionally, the nucleotide strand of interest has the sequence length ≥20 nt; and optionally, the nucleotide strand of interest has the sequence length ≥50 nt.

16. The synthesizing method according to claim 3, wherein the nucleotide strand of interest has a sequence length ≥2 nt;

optionally, the nucleotide strand of interest has the sequence length ≥20 nt; and optionally, the nucleotide strand of interest has the sequence length ≥50 nt.

17. The synthesizing method according to claim 2, wherein reaction duration of the synthesizing method is ≥5 min optionally, the reaction duration of the synthesizing method ranges from 5 min to 16 h; and optionally, the reaction duration of the synthesizing method ranges from 1 h to 16 h.

18. The synthesizing method according to claim 3, wherein reaction duration of the synthesizing method is ≥5 min optionally, the reaction duration of the synthesizing method ranges from 5 min to 16 h; and optionally, the reaction duration of the synthesizing method ranges from 1 h to 16 h.

19. The synthesizing method according to claim 2, wherein the nucleotide strand of interest comprises linear and/or circular nucleotide strand;

optionally, the nucleotide strand of interest is any one or more of RNA single strand, RNA duplex, DNA/RNA hybrid single strand and DNA/RNA hybrid duplex; and optionally, the synthesizing method further comprises isolating and purifying a ligated product, so as to obtain the nucleotide strand of interest.

20. The synthesizing method according to claim 3, wherein the nucleotide strand of interest comprises linear and/or circular nucleotide strand;

optionally, the nucleotide strand of interest is any one or more of RNA single strand, RNA duplex, DNA/RNA hybrid single strand and DNA/RNA hybrid duplex; and optionally, the synthesizing method further comprises isolating and purifying a ligated product, so as to obtain the nucleotide strand of interest.

* * * * *